United States Patent
Huang (10) Patent No.: US 7,764,003 B2
(45) Date of Patent: Jul. 27, 2010

(54) SIGNAL CONTROL IN MICROMACHINED ULTRASONIC TRANSDUCER

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 549 days.

(21) Appl. No.: 11/695,919

(22) Filed: Apr. 3, 2007

(65) Prior Publication Data

US 2007/0228877 A1    Oct. 4, 2007

Related U.S. Application Data

(60) Provisional application No. 60/744,242, filed on Apr. 4, 2006.

(51) Int. Cl.
  H02N 2/00   (2006.01)
  A61B 8/00   (2006.01)
  B06B 1/06   (2006.01)
  G01H 17/00  (2006.01)

(52) U.S. Cl. ............... 310/309; 600/437; 367/140; 73/570

(58) Field of Classification Search ............ 310/309; 600/437, 459; 367/140; 73/570
See application file for complete search history.

(56) References Cited

U.S. PATENT DOCUMENTS

| | | | |
|---|---|---|---|
| 6,945,115 B1 | 9/2005 | Wang | |
| 2002/0048220 A1* | 4/2002 | Khuri-Yakub et al. | 367/181 |
| 2003/0039173 A1 | 2/2003 | Yurchenko et al. | |
| 2003/0149363 A1 | 8/2003 | Dreschel et al. | |
| 2004/0267134 A1 | 12/2004 | Hossack et al. | |
| 2005/0075572 A1 | 4/2005 | Mills et al. | |
| 2005/0101867 A1 | 5/2005 | Johnson et al. | |
| 2005/0146240 A1 | 7/2005 | Smith et al. | |
| 2006/0173342 A1* | 8/2006 | Panda et al. | 600/459 |
| 2006/0273805 A1* | 12/2006 | Peng et al. | 324/686 |
| 2007/0083119 A1* | 4/2007 | Adachi et al. | 600/437 |
| 2007/0287918 A1* | 12/2007 | Huang | 600/459 |
| 2009/0048522 A1* | 2/2009 | Huang | 600/459 |

* cited by examiner

*Primary Examiner*—Thomas M Dougherty
(74) *Attorney, Agent, or Firm*—Lee & Hayes, PLLC (57) ABSTRACT

A capacitive micromachined ultrasonic transducers (cMUT) uses signal control methods to reduce harmonic distortion of the output signal. The method uses an AC transmission input signal characterized with a frequency $\omega$ and takes the second-order frequency component with frequency $2\omega$, rather than the first-order frequency component with the base frequency $\omega$, as the desired output pressure signal. A frequency $\omega$ is preferably equal to $\omega_0/2$, where $\omega$ is the desired cMUT output frequency. Various examples of AC transmission input signals, in combination with or without a DC bias signal, that are suitable for producing a large second-order frequency component and small (ideally zero) first-order frequency component are disclosed.

20 Claims, 8 Drawing Sheets

SIGNAL CONTROL IN MICROMACHINED ULTRASONIC TRANSDUCER

PRIORITY

This application claims priority from U.S. Provisional Applications Ser. No. 60/744,242, filed Apr. 4, 2006.

BACKGROUND

The present invention relates capacitive micromachined ultrasonic transducers (cMUT), particularly to methods for operating cMUT.

Capacitive micromachined ultrasonic transducers (cMUTs) are electrostatic actuator/transducers, which are widely used in various applications. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

The basic structure of a cMUT is a parallel plate capacitor with a rigid bottom electrode and a top electrode residing on or within a flexible membrane, which is used to transmit (TX) or detect (RX) an acoustic wave in an adjacent medium. A DC bias voltage is applied between the electrodes to deflect the membrane to an optimum position for cMUT operation, usually with the goal of maximizing sensitivity and bandwidth. During transmission an AC signal is applied to the transducer. The alternating electrostatic force between the top electrode and the bottom electrode actuates the membrane in order to deliver acoustic energy into the medium surrounding the cMUT. During reception the impinging acoustic wave vibrates the membrane, thus altering the capacitance between the two electrodes. An electronic circuit detects this capacitance change.

Figure 1:
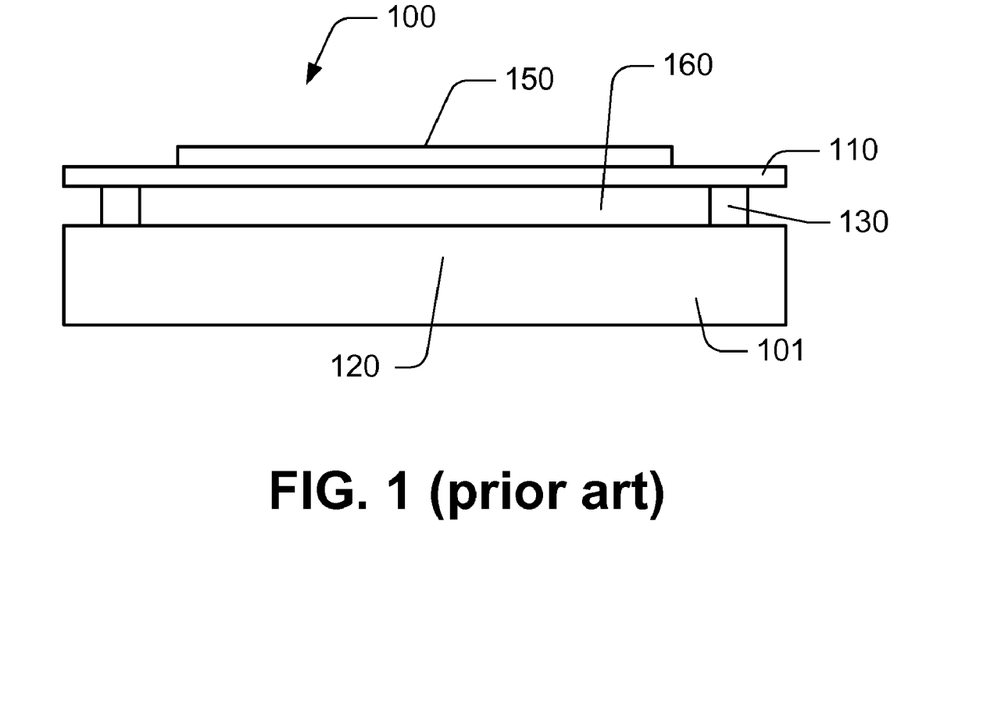
FIG. 1 is a schematic cross-sectional view of a conventional flexible membrane cMUT.

Two representative types of cMUT structures are conventional flexible membrane cMUT and the newer embedded-spring cMUT (EScMUT). FIG. 1 shows a schematic cross-sectional view of a conventional flexible membrane cMUT 10, which has a fixed substrate 101 having a bottom electrode 120, a flexible membrane 110 connected to the substrate 101 through membrane supports 130, and a movable top electrode 150. The flexible membrane 110 is spaced from the bottom electrode 120 by the membrane supports 130 to form a transducing space 160.

Figure 2:
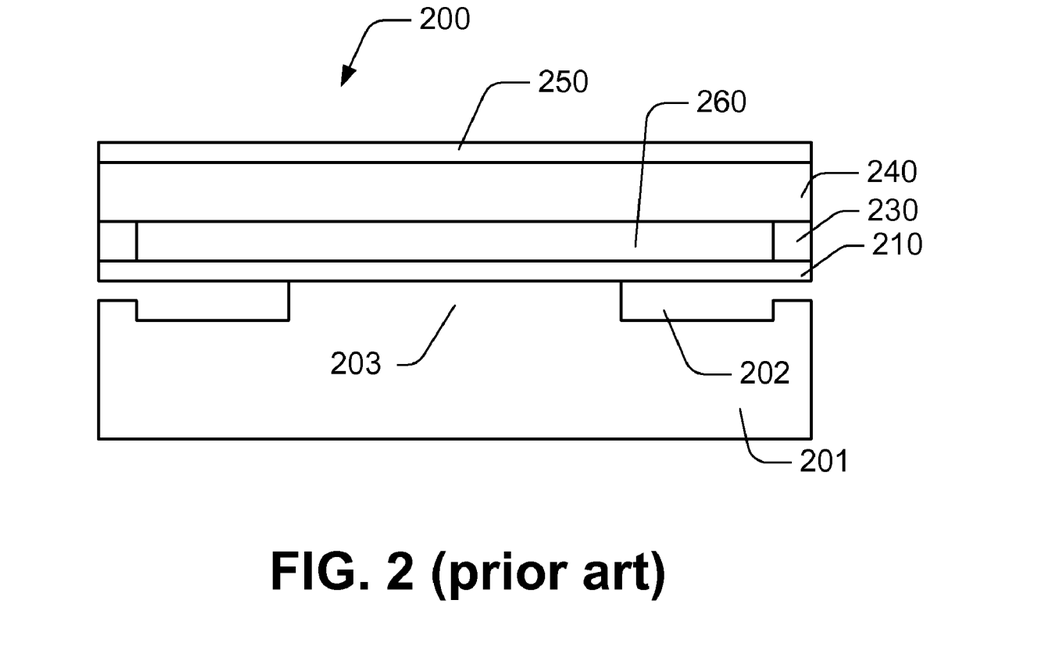
FIG. 2 is a schematic cross-sectional view of embedded-spring cMUT (EScMUT).

FIG. 2 is a schematic cross-sectional view of embedded-spring cMUT (EScMUT) 200, which is described in the PCT International Application No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006, particularly the cMUTs shown in FIGS. 5A-5D therein. The cMUT 200 has a substrate 201, on top of which is a spring anchor 203 supporting a spring layer 210; a surface plate 240 connected to the spring layer 210 through spring-plate connectors 230; and a top electrode 250 connected to the surface plate 240. The cMUT 200 may be only a portion of a complete cMUT element (not shown).

Figure 3A:
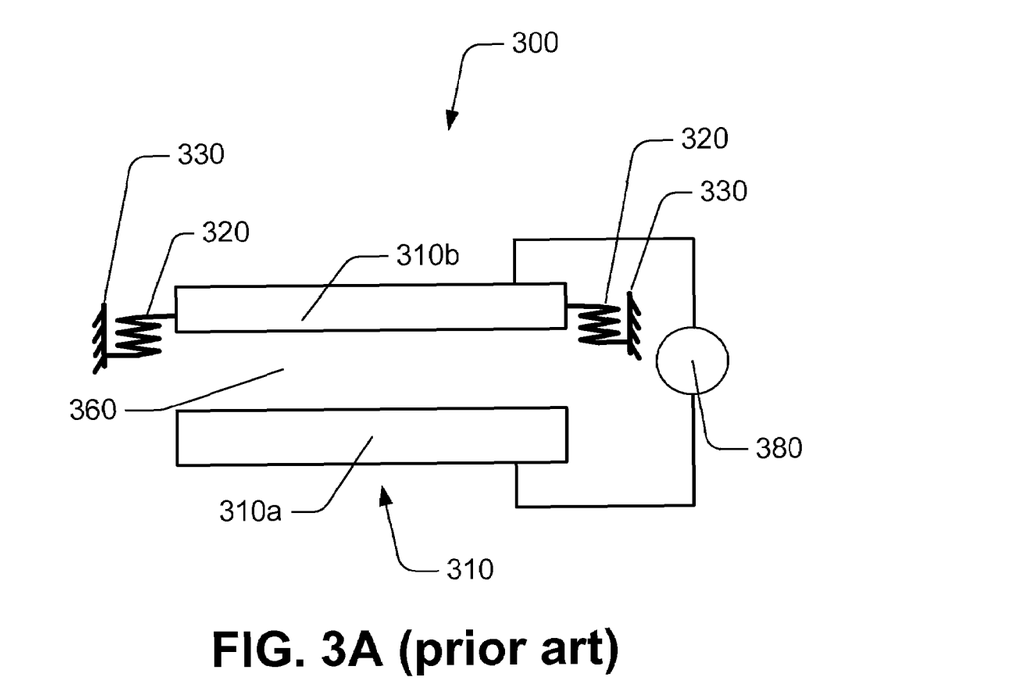
FIG. 3A shows a simplified schematic cMUT model
Figure 3B:
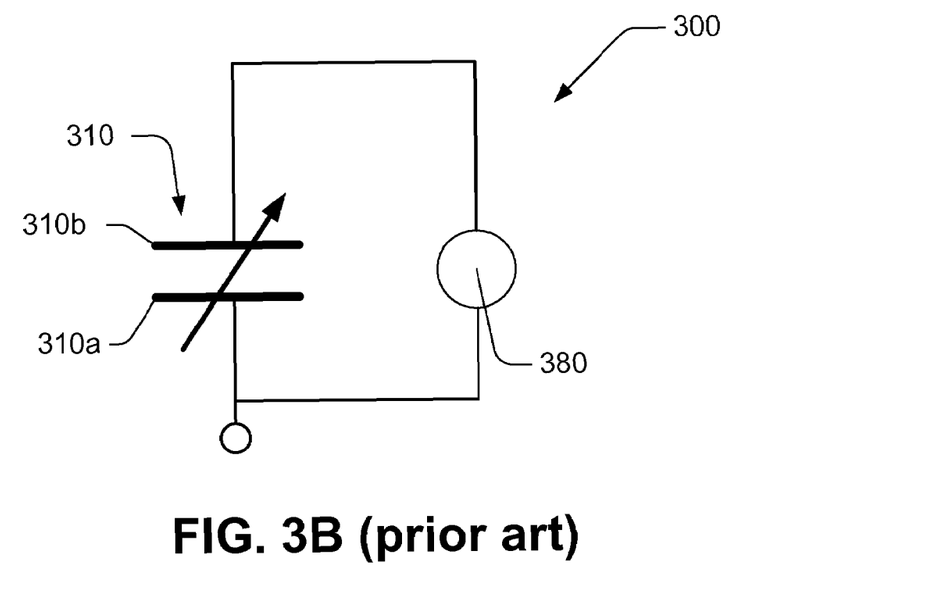
FIG. 3B shows a further simplified circuit model having a variable capacitor representing a cMUT.

Although structurally and mechanically very different, cMUTs 100 and 200 in FIGS. 1-2, and most other cMUTs, can be commonly represented by a simplified schematic model. FIG. 3A shows a simplified schematic cMUT model 300 which shows capacitor 310 consisting of fixed electrode 310a and movable electrode 310b, which is connected to equivalent springs 320 anchored by spring anchors 330. The fixed electrode 310a and the mobile electrode 310b define transducing space 360 therebetween. The electrodes 310a and 310b are connected to an interface circuit 380. The cMUT model can be further simplified as a circuit model having a variable capacitor as shown in FIG. 3B. The variable capacitor 310 in FIG. 3B has two electrodes 310a and 310b and is connected to the interface circuit 380.

Essentially all cMUTs based on a variable capacitor, even comb driver cMUTs in which the movable electrode is laterally displaced (along the direction of the electrode surface), may be represented by the variable capacitor model 300 shown in FIG. 3B. In this description, the variable capacitor model 300 shown in FIG. 3B is be used to represent any cMUT regardless of its structural and mechanical characteristics.

Usually a cMUT is biased with a DC voltage either directly or through a bias circuit. The cMUT also connects to an interface circuit, which usually comprises a switch, a transmission (TX) port and a reception (RX) port. In transmission, a transmission input signal is applied on the cMUT through the transmission port to move a movable electrode of the cMUT, which in turn energizes the medium and transmit acoustics energy into the medium. In reception, acoustic energy impinging on the cMUT is detected electrically by an interface circuit through the reception port. The switch switches the connection of the cMUT to either transmission port or reception port during operation.

One problem cMUT operation often has is the high-frequency harmonic distortion in the signal. The problem is explained as follows. If the transmission input signal is $V_{tx}(t)$, and the DC bias is $V_{dc}$, the voltage V applied on the cMUT is $V=V_{dc}+V_{tx}(t)$. The electrostatic force/pressure applied on the cMUT is proportional to $V^2$:

$$\text{Pressure} \propto V^2 = (V_{dc}+V_{tx})^2 = V_{dc}^2 + 2V_{tx}V_{dc} + V_{tx}^2.$$

In the existing cMUT operation methods, the linear term $2V_{tx}V_{ac}$ is the wanted output pressure signal and the cMUT system and its operation are usually designed according to this premise. $V_{dc}$ may be set to bias the cMUT to a desired operation point. The transmission input signal $V_{tx}(t)$ is usually an AC signal which has a frequency matching the cMUT operating frequency $\omega$:

$$V_{tx}(t) = V_{ac}\sin(\omega t) = (V_{p-p}/2)\sin(\omega t),$$

where $V_{ac}$ and $V_{p-p}$ are the amplitude and peak-peak voltage of the applied AC signal, respectively; ω is the operation frequency of the cMUT. The electrostatic force/pressure is then expressed as:

$$\text{Pressure} \propto (V_{dc} + V_{tx})^2 = \left(V_{dc}^2 + \frac{V_{p-p}^2}{8}\right) + V_{p-p}V_{dc}\sin(\omega t) - \frac{V_{p-p}^2}{8}\cos(2\omega t)$$

where $$\left(V_{dc}^2 + \frac{V_{p-p}^2}{8}\right)$$

is a DC term used for DC bias, $V_{p-p}V_{dc}\sin(\omega t)$ is the wanted output pressure signal at the cMUT operating frequency ω, while $$-\frac{V_{p-p}^2}{8}\cos(2\omega t)$$

is the undesired second harmonic distortion. Because a large $V_{p-p}$ is generally needed to generate a large enough output pressure, the existing actuation methods usually have a significant second harmonic that may distort the output pressure. For example, if $V_{p-p}=2V_{dc}$, then:

$$\text{Pressure} \propto (V_{dc} + V_{tx})^2 = \frac{3}{8}V_{p-p}^2 + \frac{V_{p-p}^2}{2}\sin(\omega t) - \frac{V_{p-p}^2}{8}\cos(2\omega t)$$

In this case, the second harmonic is comparable to the output pressure signal at the fundamental operating frequency ω. This type of distortion may make it difficult to use cMUT to do applications such as Tissue Harmonic Imaging (THI). Therefore, new method is needed to improve cMUT operation.

SUMMARY OF THE DISCLOSURE

This application discloses capacitive micromachined ultrasonic transducers (cMUT) using signal control methods to reduce harmonic distortion of the output signal are described. Both the signal control method and cMUT systems implementing the signal control method are described.

The method uses an AC transmission input signal characterized with a frequency ω. Instead of using the first-order frequency component with the inherent base frequency ω as the desired output pressure signal, the method takes the second-order frequency component with frequency 2ω as the wanted output pressure signal. In one embodiment, the AC transmission input signal is characterized with a frequency ω=ω/2, where $ω_0$ is the desired cMUT output frequency. In this case, the second-order frequency component has a frequency 2ω which is $2(ω_0/2)=ω_0$, the desired cMUT output frequency. Various examples of AC transmission input signals, in combination with or without a DC bias signal, that are suitable for producing a large second-order frequency component and small (ideally zero) first-order frequency component are described.

One aspect of the method is to use an AC transmission input signal without a DC bias signal in cMUT transmission operation, and apply the DC bias in cMUT reception operation only. The DC bias is switched on or connected only when the cMUT system is in reception operation. The unmixed AC transmission input signal without a DC bias results in a clean output pressure signal at frequency 2ω.

Another aspect of the method is to use a shifted AC transmission input signal $V_{tx}(t)+V_{dc}$ or $V_{tx}(t)-V_{dc}$, which when combined with a DC bias voltage $V_{dc}$ on one of the electrodes of the cMUT result in a net AC transmission input signal $V_{tx}(t)$.

In one embodiment, an absolute-value signal |Vtx(t)| is used as the transmission AC signal to increase the level of the output pressure signal, where $V_{tx}(t)$ is any suitable signal for the second-order frequency method described herein. The method may include a voltage level shift to shift the voltage of the absolute-value signal |Vtx(t)| and then amplify the shifted absolute-value signal to a desired amplitude (e.g., the maximum amplitude allowed by the power supply of the system). The amplified absolute-value signal is then applied with a proper DC bias on the cMUT to achieve optimal performance.

DETAILED DESCRIPTION

The micromachined ultrasonic transducer using signal control methods for reducing harmonic distortion of the output signal are described in detail along with the figures, in which like parts are denoted with like reference numerals or letters. The methods are adapted for transmitting an ultrasonic signal and/or receiving a pressure signal using a cMUT system.

CMUT Configurations for Second-Order Frequency Method

Figure 4:
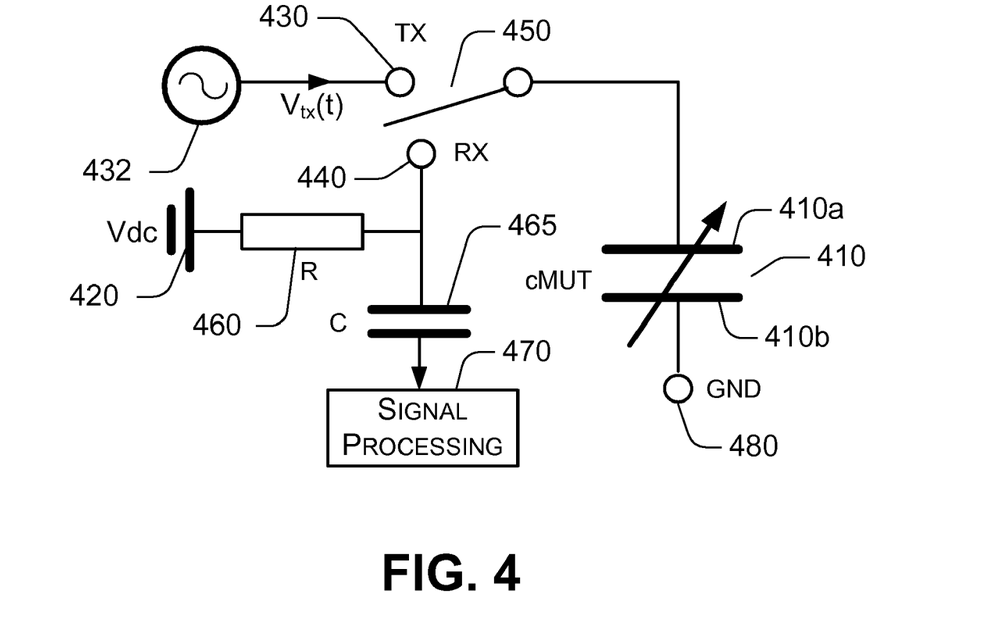
FIG. 4 shows an exemplary cMUT with an unmixed AC transmission input signal without a DC bias signal in the transmission mode.

FIG. 4 shows an exemplary cMUT with an unmixed AC transmission input signal without a DC bias signal in the transmission mode. The setup includes cMUT 410 which is represented by a variable capacitor. One electrode 410a of the cMUT 410 is connected to transmission (TX) port 430 and reception (RX) port 440. Switch 450 is used to switch the line between the transmission port 430 and the reception port 440. An AC transmission input signal $V_{tx}(t)$ is generated by AC signal source 432 and applied at the transmission input signal port 430, which may be a separate port, or a port integrated with the transmission input signal source 432. The detail of the pressure signal generation in transmission mode described later in this description.

A DC bias $V_{dc}$ is supplied by a DC signal source 420 and connected to the reception port (RX) 440 through a bias circuit which includes a resistor 460 and a DC decoupling capacitor 465. The DC decoupling capacitor 465 is also a part of the signal processing circuit (interface circuit) along with the signal processing unit 470. The DC decoupling capacitor 465 decouples the DC signal source 420 from the signal processing unit 470. The DC bias $V_{dc}$ is applied to the cMUT 410 only in the reception mode when the switch 450 is switched to the reception port 440. The transmission input signal $V_{tx}(t)$, the DC bias $V_{dc}$, and the switch 450 are connected to the same electrode of the cMUT 410. The other electrodes 410b of the cMUT 410 is connected to electrical ground 480.

In reception mode, the pressure signal (such as a pressure generated by an impinging ultrasonic wave) is applied to a movable electrode (410a or 410b) of the cMUT 410 to cause a motion of the movable electrode. The motion of the movable electrode generates a capacitance change of the cMUT 410. The capacities change and the voltage applied at the cMUT 410 cause an electric current signal, which is received at the reception port 440 and sent to signal processing unit 470.

In transmission mode, the switch 450 is switched to the transmission port 430 (TX). The DC bias $V_{dc}$ is disconnected from the cMUT 410 in transmission mode. The transmission input signal $V_{tx}(t)$ alone, unmixed with the DC bias $V_{dc}$, is applied to the cMUT system at the transmission port 430. In other words, the transmission mode the final transmission input signal applied on the cMUT 410 is solely contributed by the transmission input signal $V_{tx}(t)$ generated by AC signal source 432 without applying a separate DC bias voltage $V_{dc}$ in.

The cMUT 410 responds to the transmission input signal $V_{tx}(t)$ and generates electrostatic force which is an output pressure exerted on the movable electrode of cMUT 410. The movable electrode then energizes the medium (not shown) in which the cMUT 410 is placed to generate an acoustic wave, such as an ultrasonic wave. The transmission mode may also be used as an actuation mode in which the cMUT generates a motion of its movable electrode in response to the transmission input signal $V_{tx}(t)$. The motion of the movable electrode can be used for actuating a component which is either directly connected to the movable electrode or indirectly connected to the movable electrode through a medium.

The cMUT setup of the FIG. 4 is only one of the many ways to achieve a desired transmission input signal applied on the cMUT. The goal is to effectuate a net voltage across the two electrodes of the cMUT such that the net voltage (the transmission input signal) $V_{tx}(t)$ yields an output pressure signal proportional to $V_{tx}(t)^2$ that has a large second-order frequency component and a small first-order base frequency component. Many other configurations may be used to achieve this goal. For example, instead of connecting $V_{dc}$ directly with the reception port 440 as show in FIG. 4, $V_{dc}$ may be connected to the cMUT 410 either directly or through a circuit and is switched on and off between the reception mode and the transmission mode using a separate switch other than the switch 450. Such a configuration may increase the complexity of the circuit and therefore may be less preferred than the configuration shown in FIG. 4, but is nonetheless possible and maybe desired due to other considerations.

Alternatively, a shifted AC transmission input signal $V_{tx}(t)+V_{dc}$ or $V_{tx}(t)-Vdc$, which when combined with a DC bias voltage Vdc on one of the electrodes of the cMUT result in a net AC transmission input signal $V_{tx}(t)$. $V_{tx}(t)$ is selected such that it is suited for producing a large second-order frequency component and a small (ideally zero) first-order frequency component.

Figure 5:
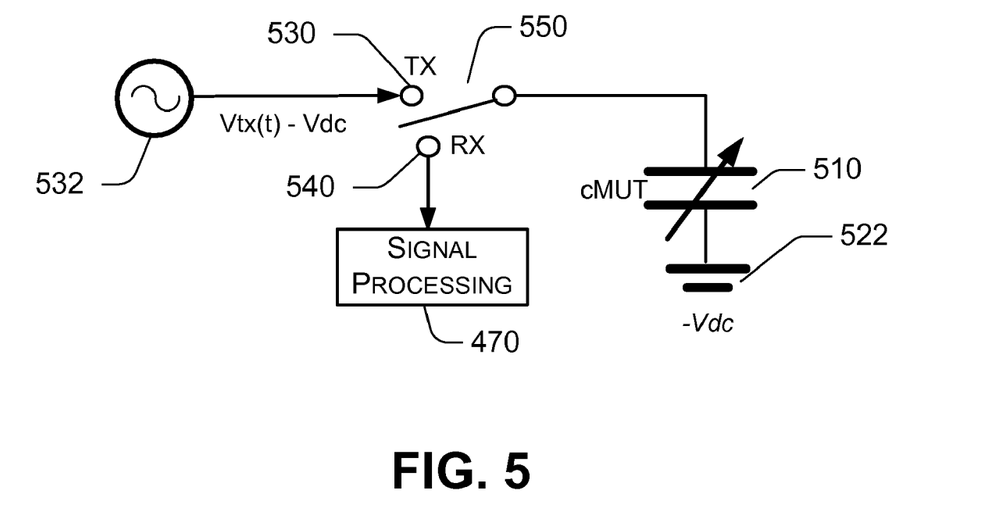
FIG. 5 shows an example of using a shifted AC transmission input signal combined with a DC bias.

FIG. 5 shows an example of using a shifted AC transmission input signal combined with a DC bias. The setup includes cMUT 510 which is represented by a variable capacitor. One electrode of the cMUT 510 is connected to transmission (TX) port 530 and reception (RX) port 540. Switch 550 is used to switch the line between the transmission port 530 and the reception port 540. A shifted AC transmission input signal $V_{tx}(t)-V_{dc}$ is supplied by AC signal source 532 and applied at the transmission input signal port 530. A DC bias $V_{dc}$ is provided by a DC signal source 522 connected to the other electrode of the cMUT 510. The DC bias $V_{dc}$ is applied to the cMUT 510 in both the transmission mode and the reception mode.

In transmission mode, the switch 550 is switched to the transmission port 530 (TX). The shifted transmission input signal $V_{tx}(t)-V_{dc}$ is compensated by the DC bias $-V_{dc}$ (as they are applied to the opposite electrodes) to result in a net transmission input signal $V_{tx}(t)$ applied on the cMUT 510.

Figure 6:
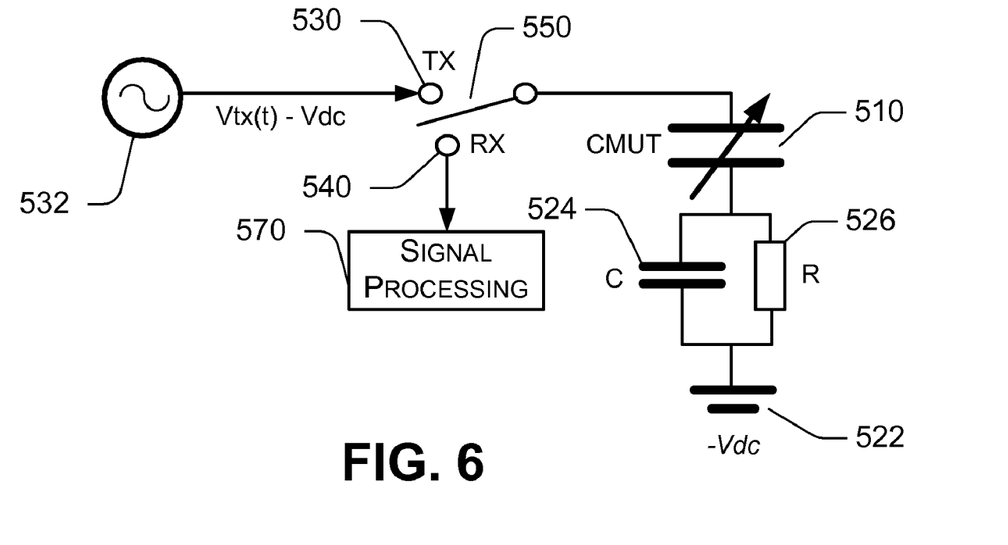
FIG. 6 shows another example of using a shifted AC transmission input signal combined with a DC bias.

FIG. 6 shows another example of using a shifted AC transmission input signal combined with a DC bias. The cMUT setup is similar to the cMUT setup of FIG. 5 except that the DC bias $V_{dc}$ of FIG. 6 is connected to the cMUT 510 through a bias circuit consisting of capacitor 524 and resistor 526 in parallel.

Figure 7:
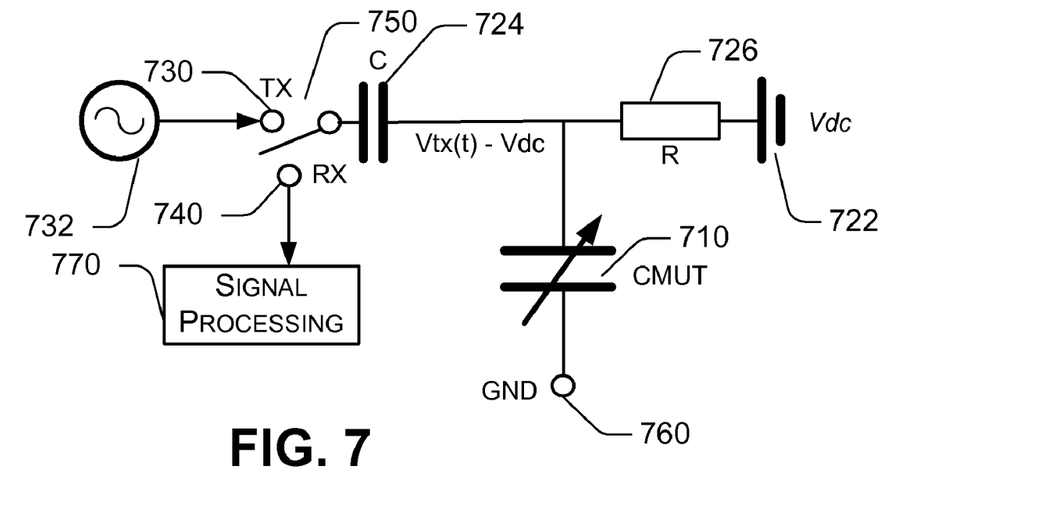
FIG. 7 shows another example of using a shifted AC transmission input signal combined with a DC bias.

FIG. 7 shows another example of using a shifted AC transmission input signal combined with a DC bias. The setup includes cMUT 710 which is represented by a variable capacitor. One electrode of the cMUT 710 is connected to transmission (TX) port 730 and reception (RX) port 740 through capacitor 724. Switch 750 is used to switch the line between the transmission port 730 and the reception port 740. A shifted AC transmission input signal is supplied by AC signal source 732 and applied at the transmission input signal port 730, which is connected to the same electrode of the cMUT 710. A DC bias $V_{dc}$ is provided by a DC signal source 722 connected to the same electrode of the cMUT 710 through resister 726. The DC bias $V_{dc}$ is applied to the cMUT 710 in both the transmission mode and the reception mode. The other electrode of the cMUT 710 is connected to ground 760.

In transmission mode, the switch 750 is switched to the transmission port 730 (TX). Due to the existence of the decoupling capacitor 724, the actual shifted transmission input signal applied at the cMUT 710 may be different from the shifted transmission input signal supplied by the AC signal source 732. Design consideration is therefore given to ensure that the shifted transmission input signal after the decoupling capacitor 724 is $V_{tx}(t)-V_{dc}$. This signal is added to the DC bias $V_{dc}$ (as they are applied to the same electrode) to result in a net transmission input signal $V_{tx}(t)$ applied on the cMUT 710.

Second-Order Frequency Method

According to one aspect of the method described herein, the second-order frequency component of the output pressure signal, rather than the conventional first-order frequency component, is taken as the signal. This choice results in certain requirements for the choices of the transmission input signal such that the resultant second-order frequency component is suited to be the desired output pressure signal.

In transmission mode, the electrostatic force (output pressure) exerted on the movable electrode of the cMUT is proportional to $V_{tx}(t)^2$, where $V_{tx}(t)$ represents the final (net) transmission input signal applied on the cMUT. Preferably, no DC bias $V_{dc}$ is present in the final (net) transmission input signal in the transmission mode. Therefore, the output pressure is generated from the term $V_{tx}(t)^2$ instead of $2 V_{dc} V_{tx}(t))$ as that in the existing cMUT operation methods.

Various AC transmission input signals $V_{tx}(t)$ may be used. The signal selection for the transmission input signal $V_{tx}(t)$ is a design consideration of the cMUT system described herein as the output pressure depends on the characteristics of the transmission input signal $V_{tx}(t)$.

Figure 8:
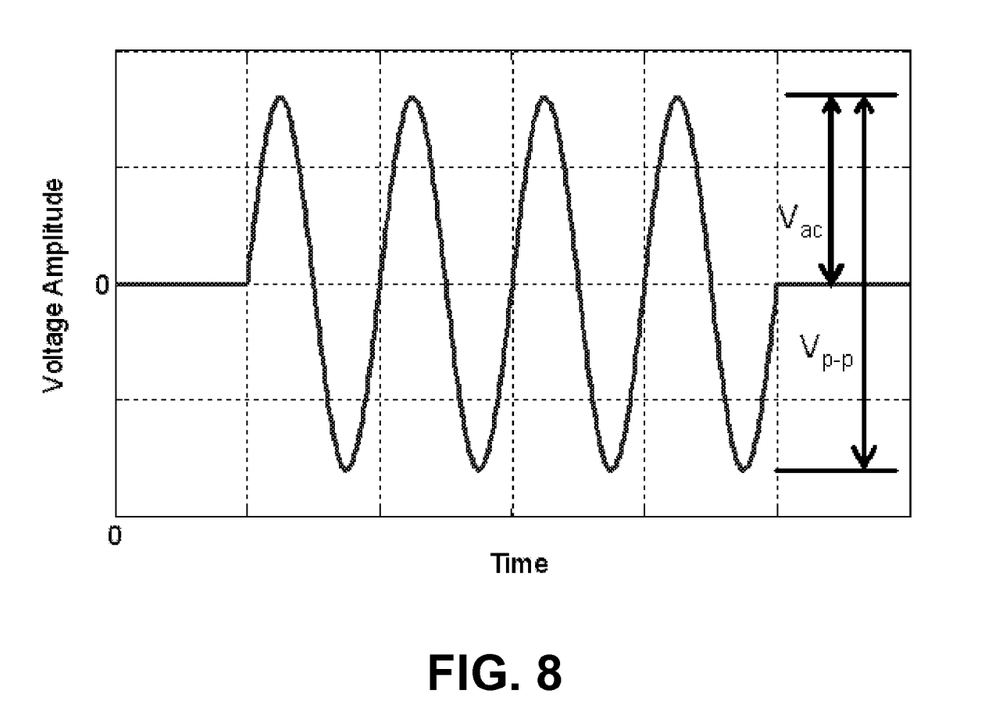
FIG. 8 is a diagram of an example of a suitable transmission input signal having a sine wave.

FIG. 8 shows an example of a suitable transmission input signal, which is a sine wave:

$$V_{tx}(t) = V_{ac}\sin(\omega t) = (V_{p\text{-}p}/2)\sin(\omega t),$$

where $V_{p\text{-}p}$ is the peak-to-peak voltage, and $V_{tx}(t)$ does not have a DC bias component (or a $V_{dc}$ component is included in the original $V_{tx}(t)$ but is canceled by an applied DC bias $V_{dc}$).

The transmission input signal $V_{tx}(t)$ defines an output signal function $V_{tx}(t)^2$, and the output pressure is proportional to the output signal function $V_{tx}(t)^2$:

$$\text{pressure} \propto (V_{tx}(t))^2 = \frac{V_{p\text{-}p}^2}{8} - \frac{V_{p\text{-}p}^2}{8}\cos(2\omega t)$$

Figure 9:
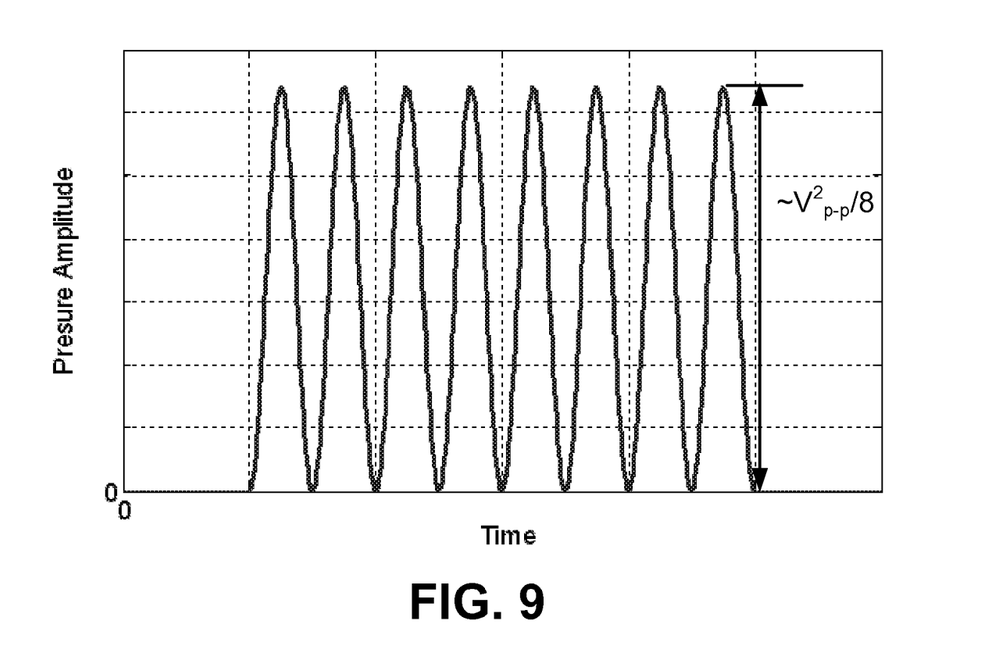
FIG. 9 is a diagram of an AC component of the output pressure signal generated by the transmission input signal of FIG. 8.

The above pressure has an effective DC bias term $$\frac{V_{p\text{-}p}^2}{8}$$

and an AC signal component $$\frac{V_{p\text{-}p}^2}{8}\cos(2\omega t),$$

which is a second-order frequency component and is shown in FIG. 9. It is important to note that with this choice of transmission input signal $V_{tx}(t)$, there is no first-order frequency component at the base frequency ω of the transmission input signal $V_{tx}(t)$. Instead, the second-order frequency component $$\frac{V_{p\text{-}p}^2}{8}\cos(2\omega t)$$

is taken as the output pressure signal. There is further no other higher frequency harmonic components. As a result, the output pressure signal is not distorted.

Figure 10:
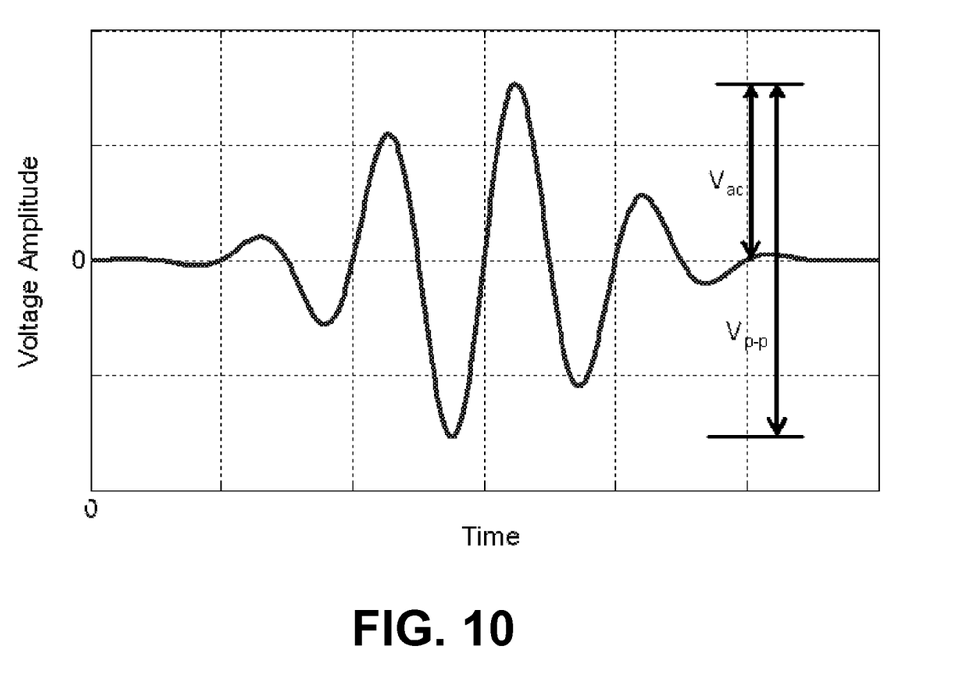
FIG. 10 is a diagram an example of Gaussian-shaped signal as transmission input signal.

Another exemplary transmission input signal is Gaussian-shaped sine signals. FIG. 10 shows an example of Gaussian-shaped input signal, which may be written as:

$$V_{tx}(t) = \frac{V_{p\text{-}p}}{2}\sin(\omega t) * \exp\left(\frac{-(t-t_o)^2}{2\sigma^2}\right)$$

The above signal is also suitable as a transmission input signal of the second-order frequency method, as $V_{tx}(t)^2$ would only have a second-order frequency component at double frequency 2ω, and no first-order frequency component at the base frequency ω.

In the above examples, no DC bias voltage is included in the transmission input signal $V_{tx}(t)$. This may be accomplished by either disconnecting DC bias (i.e., $V_{dc}$=0) in transmission mode as shown in FIG. 4, or applying a DC bias $V_{dc}$ to cancel the $V_{dc}$ term included in the original $V_{tx}(t)$ as shown in FIGS. 5-7. Having no DC bias voltage in the final transmission input signal $V_{tx}(t)$ resulting a zero first-order frequency component in the output pressure signal and leaves a clean second-order frequency component as the useful output pressure signal. This is a preferred condition, but not required. A presence of a very low $V_{dc}$ may result in a nonzero first-order frequency component, but as long as there is still a dominating second-order frequency component, and the transmission input signal may still be usable.

In addition to the above examples, any AC transmission input signal $V_{tx}(t)$ which may result in a usable output pressure signal based on the second-order frequency component may be used. Because the output pressure signal is proportional to $V_{tx}(t)^2$ and thus depends on the characteristics of the transmission input signal $V_{tx}(t)$, the transmission input signal $V_{tx}(t)$ is a significant part of the design consideration of the cMUT system described herein. In general, the following factors should be considered:

(1) The transmission input signal $V_{tx}(t)$ itself is not required to be a pure sine wave at a single frequency. Instead, Vtx(t) usually has a frequency distribution and a dominating component that is around a central frequency ω (which is preferably $\omega_0/2$). In particular, in practical applications it is unlikely that an uninterrupted pure sine wave at single frequency can be used as a transmission input signal. Often, even if a signal with a single fundamental frequency is used, the signal is likely to be truncated or shaped by a time window controlled by on and off gates. For example, a real transmission input signal may be expressed as $V_{tx}(t)=W(t)\times S_{tx}(t)$, where W(t) is a gated time window, and $S_{tx}(t)$ is a wave signal such as a sine wave. Two common gated time windows are a square box and a Gaussian-shaped window.

(2) $V_{tx}(t)^2$ should preferably have a dominating frequency component around the double-central frequency 2ω (which is preferably $\omega_0$). This is different from the conventional methods in which both Vtx(t) and $V_{tx}(t)^2$ have their dominating frequency component around the same frequency. To be considered dominating, a frequency component should be at least twice as large, and preferably at least five times as large, and more preferably at least ten times as large, as the next largest frequency component.

(3) The output pressure signal, which is proportional to the output signal function $V_{tx}(t)^2$, should preferably have a small (ideally zero) first-order frequency component at the base frequency (ω).

(4) The output pressure signal should preferably have a large second-order frequency component at the double base frequency (2ω) of the transmission input signal to be used as the actual output signal. The second-order frequency component is preferably much greater than the first-order frequency component, such that the effect of first-order frequency component is negligible. The second-order frequency component is at least twice as much, and preferably at least five times as much, and more preferably at least ten times as much, as the next largest frequency component. Ideally, the second-order frequency component is the only appreciable AC component in the output signal function $V_{tx}(t)^2$.

(5) The frequency $2\omega$ of second-order frequency component should preferably be optimized to close to a fundamental operating frequency $\omega_0$ of the cMUT. It is appreciated that a cMUT may not have just a single operating frequency $\omega_0$, but rather an operating frequency range centered at or about the optimal operating frequency $\omega_0$. Accordingly, a design consideration for selecting the frequency $\omega$ of the transmission input signal $V_{tx}(t)$ is that $2\omega$ should preferably at least fall in the operating frequency range of the cMUT, and ideally close to the optimal operating frequency $\omega_0$.

(6) The transmission input signal may or may not have a DC component $V_{dc}$, as long as the combined transmission input signal results being an output pressure signal that satisfies the above conditions or preferences.

With a chosen transmission input signal $V_{tx}(t)$, there may be a variety of ways to apply it to the cMUT. In some embodiments, the transmission input signal is an AC signal $V_{tx}(t)$ only and has no DC bias mixed in. This can be accomplished using the exemplary cMUT system shown in the above FIG. 4, and other cMUT systems. In other embodiments, a shifted transmission input signal $V_{tx}(t)+V_{dc}$ or $V_{tx}(t)-V_{dc}$ is mixed with a DC bias $V_{dc}$ to result in a net transmission input signal $V_{tx}(t)$. This can be accomplished using the exemplary cMUT systems shown in the above FIGS. 5-7.

Half-Frequency Method

Because the output pressure signal has a frequency of $2\omega$, the frequency $\omega$ of the transmission input signal $V_{tx}(t)$ may preferably be set to be half of the frequency of the desired cMUT output pressure. In general, the desired frequency of the cMUT output pressure should be close to a fundamental or optimal operating frequency $\omega_0$ of the cMUT, or at least within an operating frequency range centered at or about the optimal operating frequency $\omega_0$ of the cMUT.

Accordingly, if the frequency $\omega$ of the transmission input signal $V_{tx}(t)$ is half of the desired operating frequency $\omega_0$ (that is, $\omega=\omega_0/2$), the output pressure is:

$$\text{pressure} \propto (V_{tx}(t))^2 = \frac{V_{p-p}^2}{8} - \frac{V_{p-p}^2}{8}\cos(\omega_0 t).$$

In this embodiment, the output pressure amplitudes of both DC component and AC component are determined by $V_{p-p}$. If more flexibility for independently adjusting the amplitudes of the DC component and AC component is needed, a transmission input signal consisting of the sum of two signals at the same frequency with a phase difference may be used. For example, $V_{tx}(t)=V_{p-p,\ 1}\sin(\omega_0 t/2)+V_{p-p,\ 2}\sin(\omega_0 t/2+\alpha)$, where $\alpha$ is the phase factor, may be used as the transmission input signal.

Gaussian-shaped sine signals shown in FIG. 10 may also be used in the half-frequency method. For example, if the frequency $\omega$ is chosen to be half of a desired cMUT operating frequency $\omega_0$, the signal would serve as a transmission input signal in the half-frequency method as follows:

$$V_{tx} = \frac{V_{p-p}}{2}\sin(\omega_0 t/2) * \exp\left(\frac{-(t-t_o)^2}{2(2\sigma)^2}\right),$$

which would result in an output signal function $V_{tx}(t)^2$ having a second-order frequency component at frequency $2\times(\omega_0/2)=\omega_0$, and no first-order frequency component and other high order harmonics.

Absolute-Value Signal Method

Although free of distortion, the above embodiments of the second-order frequency method may have an output pressure signal smaller than the first-order pressure signal in conventional methods that mix both $V_{dc}$ and $V_{tx}$ for a given maximum voltage supplied by the system. For example, in a conventional cMUT operating system where $V_{dc}$ is half of $V_{p-p}$ (i.e., $V_{p-p}=2V_{dc}$), the amplitude of the first-order pressure signal is $V_{p-p}^2/2$, significantly higher than the output pressure amplitude $V_{p-p}^2/8$ of the above described embodiments of the second-order frequency method for a given $V_{p-p}$ value. Often, the peak-to-peak voltage $V_{p-p}$ may be limited by the system, especially the power supply of the system.

In order to improve the output pressure generated by a given $V_{p-p}$ signal, an absolute-value signal method is introduced.

Since the electrostatic force is proportional to $V_{tx}(t)^2$, both an input signal $V_{tx}(t)$ and an input signal $|V_{tx}(t)|$ (absolute value) generate the same amount of electrostatic force. However, given the same $V_{p-p}$, the input signal $|V_{tx}(t)|$ has an effective signal amplitude that is twice as high as that of $V_{tx}(t)$ if $V_{tx}(t)$ has the same swing in both voltage polarities. Therefore, using $|V_{tx}(t)|$ to replace $V_{tx}(t)$ increases the output pressure with a given peak-to-peak value of the input signal.

Figure 11:
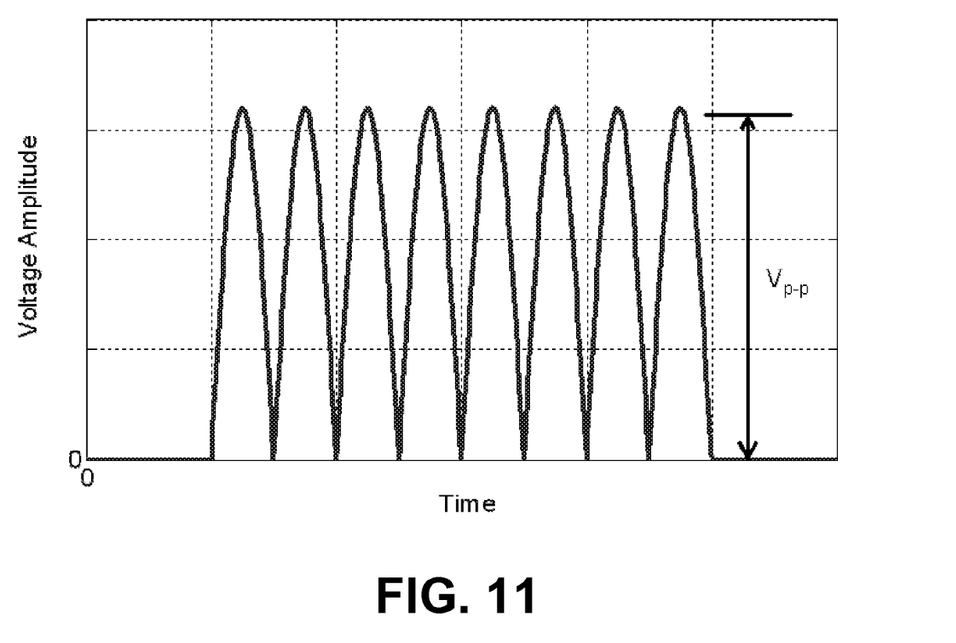
FIG. 11 is a diagram of an exemplary absolute-value signal used as transmission input signal.

FIG. 11 shows an example of absolute-value signal used as a transmission input signal. In this example, $V_{tx}(t)=2V_{p-p}\times\text{abs}(\sin(\omega t))$. The pressure output using this $V_{tx}(t)$ as the transmission input signal is:

$$\text{pressure} \propto (V_{tx})^2 = \frac{V_{p-p}^2}{2} - \frac{V_{p-p}^2}{2}\cos(2\omega t)$$

Figure 12:
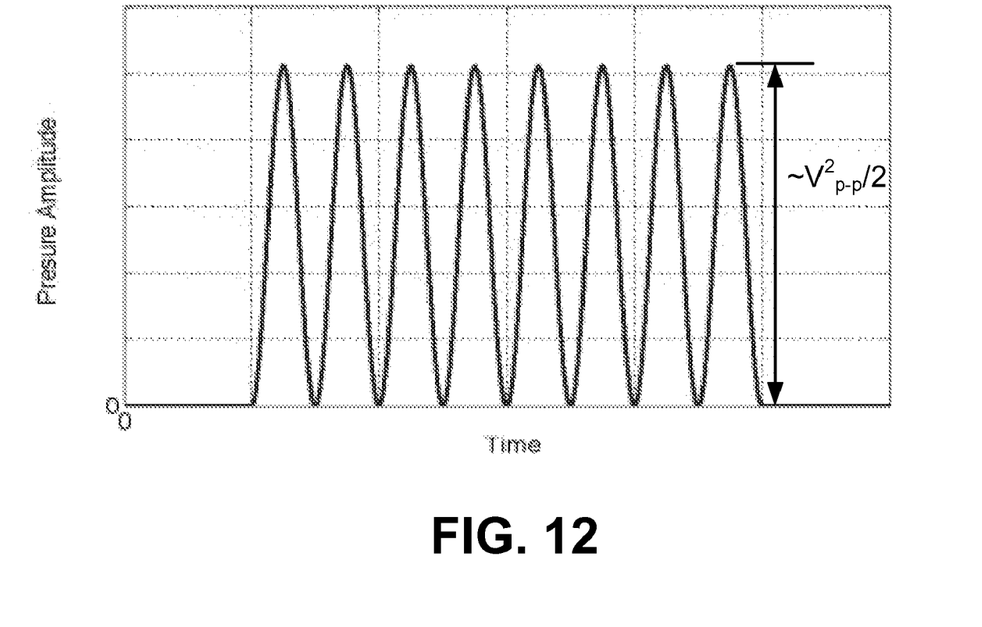
FIG. 12 is a diagram of an AC component of the output pressure signal generated by the transmission input signal of FIG. 11.

The pressure output still has the benefit of non-distorted output signal (by virtue of being free of first-order frequency component and other higher frequency harmonics), but the maximum output pressure generated by this method is much higher than the example of FIGS. 8-9 and is comparable to that of the conventional first-order frequency methods. The above pressure output is illustrated in FIG. 12.

In general, if a signal is suitable for the second-order frequency method described above or the half-frequency method, its absolute-value form would also be suitable for the absolute-value signal method but with the benefit of greater pressure output for a given peak-to-peak voltage $V_{p-p}$.

One alternative example of absolute-value signal is a transmission input voltage consisting of the sum of two absolute-value signals with a phase difference. For example, a transmission input signal $V_{tx}(t)=V_{p-p,\ 1}\times\text{abs}(\sin(\omega t))+V_{p-p,\ 2}\times\text{abs}(\sin(\omega t+\alpha))$ may be used, where $\alpha$ is the phase factor, where the frequency $\omega$ is preferably a half-frequency of a desired cMUT operating frequency $\omega_0$ (i.e., $\omega=\omega_0/2$).

The absolute-value form of Gaussian-shaped voltage signals are other examples suitable for the absolute-value signal method.

Figure 13:
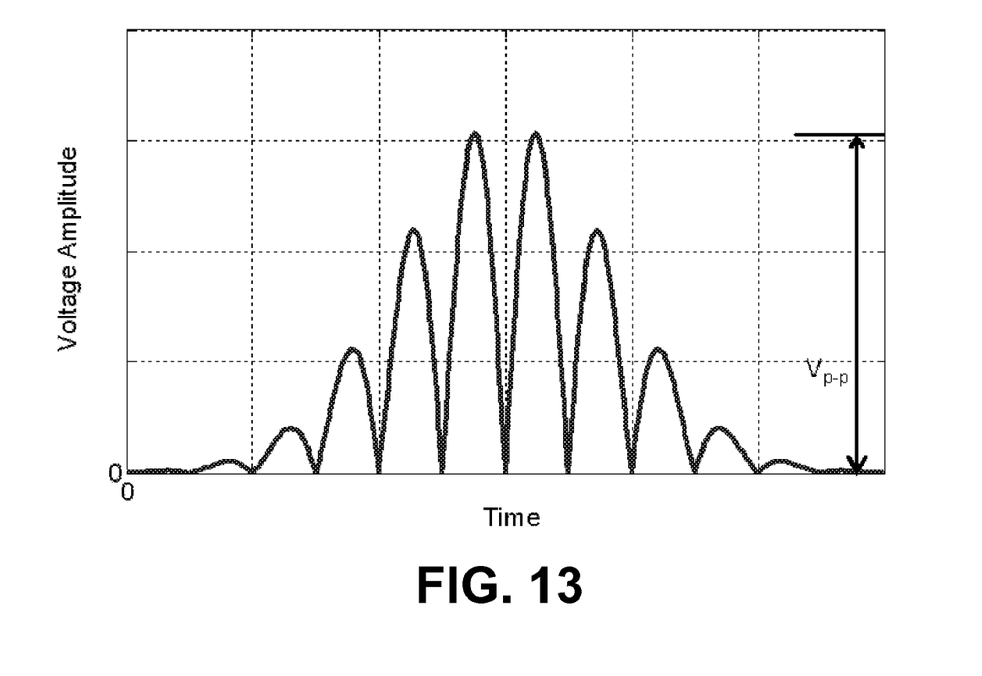
FIG. 13 is a diagram of an absolute-value Gaussian-shaped voltage signal that can be used as the transmission input signal.

FIG. 13 shows an absolute-value Gaussian-shaped voltage input signal that can be used as a transmission input signal in the absolute-value signal method. The input voltage may be written as:

$$V_{tx} = V_{p-p} \text{abs}(\sin(\omega t)) * \exp\left(\frac{-(t-t_o)^2}{2(2\sigma)^2}\right).$$

When used in the half-frequency method, the input voltage may be written as:

$$V_{tx} = V_{p-p} \text{abs}(\sin(\omega_0 t/2)) * \exp\left(\frac{-(t-t_o)^2}{2(2\sigma)^2}\right),$$

where $\omega_0$ is the desired cMUT operating frequency.

Peak-To-Peak Voltage Extension

In the above-described absolute-value signals, $|V_{tx}|$ only uses the positive swing of the power supply, which usually has both a positive and negative swing. Since the maximum absolute-value voltage may be limited by a given power supply or system, the maximum peak-to-peak value of $|V_{tx}|$ (absolute value of $V_{tx}$) may be only half of that of $V_{tx}$ for a given maximum voltage limitation. In order to fully use the both swings of the power supply and still take advantage of the absolute-value signal method, a voltage level shift may be applied on the absolute signal (e.g. to shift $|V_{tx}|$ signal to a proper voltage level such that the signal has equal positive and negative swings), then amplify the signal to a desired amplitude. The amplified signal may be then applied on a cMUT with a proper bias to restore the absolute format of the original signal with improved maximum amplitude. This technique extends the peak-to-peak voltage of the transmission input a signal.

Figure 14:
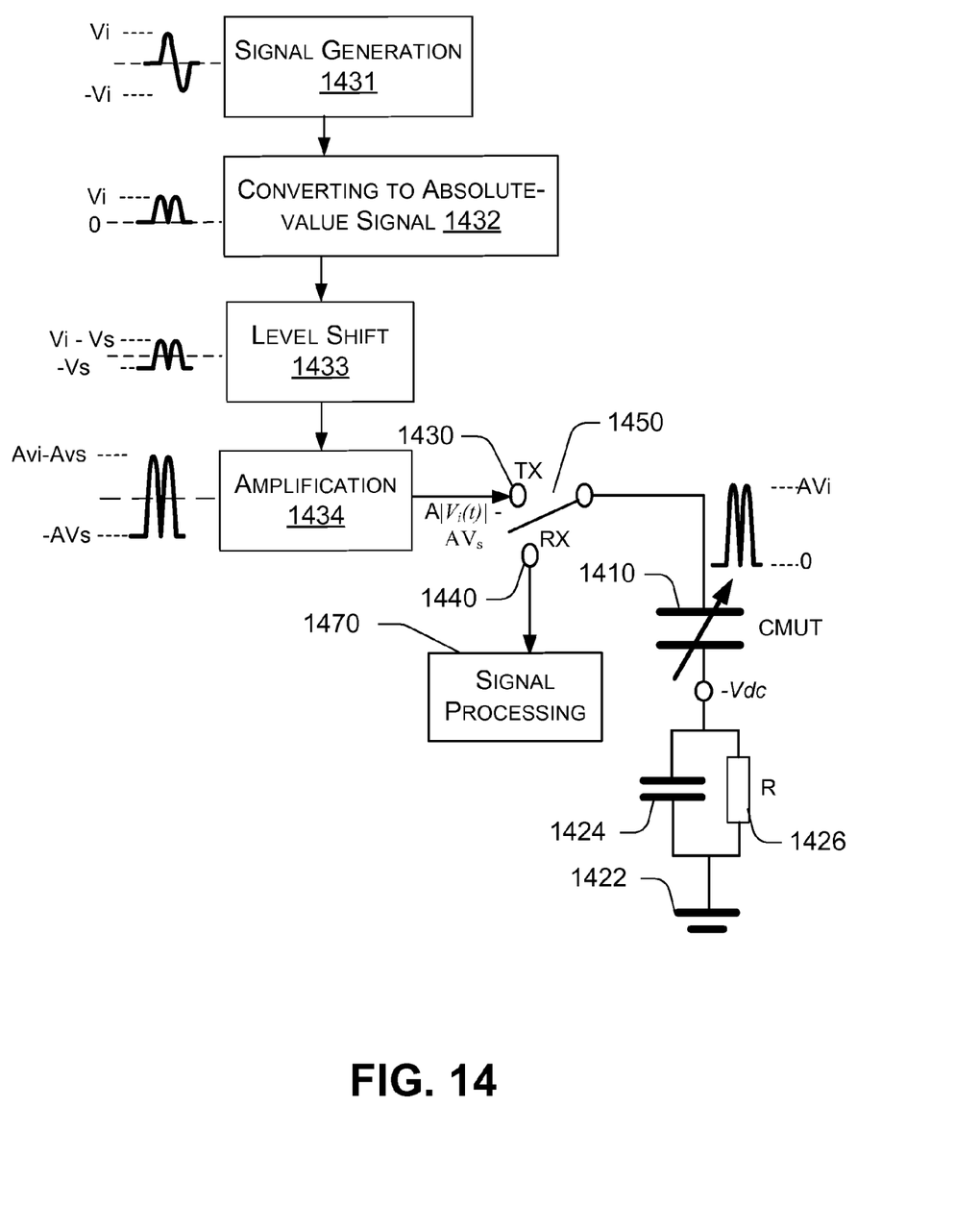
FIG. 14 shows an exemplary cMUT implementation of the peak-to-peak voltage extension technique.

FIG. 14 shows an exemplary implementation of the peak-to-peak voltage extension. In this embodiment, a desired shifted transmission input signal $V_{tx}(t)-V_{dc}$ is generated in a procedure illustrated by blocks 1431, 1432, 1433 and 1434. The shifted transmission input signal $V_{tx}(t)-V_{dc}$ (which is shown as A|Vi(t)|–AVs in FIG. 14) is then applied at transmission port 1430 in a manner similar to that illustrated in FIGS. 5-6. It is appreciated that a similar shifted transmission input signal $V_{tx}(t)-V_{dc}$ may also be applied in a manner similar to that illustrated in FIG. 7, or any other suitable manner as long as the net transmission input signal, when mixed with a DC bias $V_{dc}$ (applied either on the same electrodes or the ups and electrodes), is a $V_{tx}(t)$ signal that is suitable for the methods described in this disclosure.

The generation of shifted transmission input signal $V_{tx}(t)-V_{dc}$ is described as follows.

At block 1431, an initial signal $V_i(t)$ is generated. The fundamental characteristics of the signal such as frequency and wave shape is preferably determined at this stage according to the desired output pressure P(t) which is proportional to $V_i(t)^2$. The amplitude $V_i$ of the initial signal $V_i(t)$ may be selected for easy signal processing before amplification. Usually it may be chosen to be smaller than the maximum voltage $V_m$ that can be provided by the power supply or the system. The voltage swing at this stage is from $-V_i$ to $V_i$.

At block 1432, the initial signal $V_i(t)$ is converted to its corresponding absolute-value signal $|V_i(t)|$. The voltage swing is from 0 to $V_i$ at this stage.

At block 1433, the absolute-value signal $|V_i(t)|$ is shifted by a desired voltage level $V_s$ to result in an interim signal $V_{int}(t)=|V_i(t)|-V_s$. The voltage swing is from $-V_s$ to $V_i-V_s$ in this step. In one embodiment, $V_s$ may be chosen to be equal to $V_i/2$ in order to fully utilize the entire voltage swing in a later stage.

At block 1434, the interim signal $V_{int}(t)=|V_i(t)|-V_s$ is amplified to a desired amplitude to drive the cMUT. Assuming that the gain of the amplifier is A, the voltage signal after the amplification is $A|V_i(t)|-AV_s$, and the voltage swing is $-AV_s$ to $AV_i-AV_s$.

In one embodiment, $V_s$ is equal to $V_i/2$, while the gain A is equal to $2V_m/V_i$. In this case, the signal may be amplified to have the maximum swing (e.g., from $-V_m$ to $V_m$) that is allowed by the power supply.

The amplified voltage signal $A|V_i(t)|-AV_s$ is then applied through the transmission port 1430 to one electrodes of the cMUT 1410. As a part of the total transmission input signal, a DC bias $-V_{dc}$ is also applied to the opposite electrode of the cMUT 1410 through DC signal source 1422 and a bias circuit which includes a resistor 1426 and capacitor 1424. The bias circuit may be optional, and other forms of bias circuits, such as a simple resistor, may be used. The total (net) transmission input signal applied on the cMUT is thus $A|V_i(t)|-AV_s+V_{dc}$.

In one embodiment, $V_{dc}$ is chosen to be equal to $-AV_s$. In this case, the final (net) transmission input signal applied on the cMUT is $A|V_i(t)|$, which is the equivalent of the transmission input signal $V_{tx}(t)$ illustrated in the other examples described herein. When properly selected, $A|V_i(t)|$ may produce an output pressure with minimal distortion. If the gain A is equal to $2V_m/V_i$, the final transmission input signal $A|V_i(t)|$ may have the maximum signal swing from 0 to $2V_m$.

The embodiment of FIG. 14 may have several advantages. First, the distortion in the output pressure is minimized. Second, the transmission input signal may be amplified to fully utilize the whole swing of the power supply or the system. Third, a proper DC bias may be applied on cMUT during both transmission and reception operations, and therefore needs not to be switched on and off between the transmission mode and reception out as in the method shown in FIG. 4. This may have a benefit of a simpler cMUT system configuration and operation.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A method for operating a capacitive micromachined ultrasonic transducer (cMUT) system including a cMUT having a first electrode and a second electrode, at least one of the first electrode and the second electrode being movable and interfacing with a medium, the method comprising:

applying a transmission input signal $V_{tx}(t)$ having a base frequency $\omega$ to one of the first electrode and the second electrode of the cMUT, wherein $V_{tx}(t)$ defines an output signal function $V_{tx}(t)^2$ which has a dominating second-order frequency component having an output signal frequency $2\omega$; and allowing the movable electrode of the cMUT to move in response to the applied transmission input signal to actuate the medium.

2. The method as recited in claim 1, wherein the base frequency $\omega$ is about half of a desired operating frequency $\omega_0$ of the cMUT, such that the output signal frequency $2\omega$ is close to the desired operating frequency $\omega_0$.

3. The method as recited in claim 1, wherein the transmission input signal $V_{tx}(t)$ is solely contributed by an AC signal source without applying a separate DC bias voltage in a transmission mode.

4. The method as recited in claim 1, wherein applying a transmission input signal $V_{tx}(t)$ is enabled by switching the cMUT system to a transmission mode.

5. The method as recited in claim 1, wherein the cMUT system has a DC signal source providing a DC bias voltage which is switchably connected to one of the first electrode and the second electrode of the cMUT, the method further comprising:
disconnecting the DC bias voltage from the cMUT before applying the transmission input signal $V_{tx}(t)$.

6. The method as recited in claim 1, further comprising:
before applying the transmission input signal $V_{tx}(t)$ to the cMUT, shifting the transmission input signal to result in a shifted transmission input signal $V_{tx}(t)-V_{dc}$; and
applying a DC bias voltage $V_{dc}$ to the same electrode of the cMUT such that the net transmission input signal applied to the cMUT is $V_{tx}(t)$.

7. The method as recited in claim 1, further comprising:
before applying the transmission input signal $V_{tx}(t)$ to the cMUT, shifting the transmission input signal to result in a shifted transmission input signal $V_{tx}(t)-V_{dc}$; and
applying a DC bias voltage $-V_{dc}$ to the other electrode of the cMUT such that the net transmission input signal applied to the cMUT is $V_{tx}(t)$.

8. The method as recited in claim 1, wherein the output signal function $V_{tx}(t)^2$ has a negligible first-order frequency component of the base frequency $\omega$.

9. The method as recited in claim 1, wherein the transmission input signal $V_{tx}(t)$ comprises a component $W(t) \times V_{tx} \sin(\omega t)$, where $W(t)$ is a gated time window function.

10. The method as recited in claim 1, wherein the transmission input signal $V_{tx}(t)$ comprises a Gaussian-shaped sine signal defined as $$V_{tx}(t) = \frac{V_{p-p}}{2} \sin(\omega t) * \exp\left(\frac{-(t-t_o)^2}{2\sigma^2}\right),$$

where $V_{p-p}$ is a peak-to-peak amplitude.

11. The method as recited in claim 1, wherein the transmission input signal $V_{tx}(t)$ comprises an absolute-value signal.

12. The method as recited in claim 1, wherein the transmission input signal $V_{tx}(t)$ comprises an absolute-value signal component $W(t) \times 2V_{p-p} \times abs(\sin(\omega t))$, where $W(t)$ is a gated time window function, and $V_{p-p}$ is a peak-to-peak amplitude.

13. The method as recited in claim 1, wherein the transmission input signal $V_{tx}(t)$ comprises an absolute-value signal defined as $$V_{tx} = V_{p-p} abs(\sin(\omega t)) * \exp\left(\frac{-(t-t_o)^2}{2(2\sigma)^2}\right),$$

where $V_{p-p}$ is a peak-to-peak amplitude.

14. A method for operating a capacitive micromachined ultrasonic transducer (cMUT) system including a cMUT having a first electrode and a second electrode, at least one of the first electrode and the second electrode being movable and interfacing with a medium, the method comprising:
generating a voltage signal $V(t)$;
shifting the initial signal $V(t)$ to obtain a shifted transmission input signal $V(t)-V_{sh}$;
applying the shifted transmission input signal $V(t)-V_{sh}$ to one of the first electrode and the second electrode of the cMUT;
applying a DC bias voltage $V_{dc}$ to one of the first electrode and the second electrode of the cMUT such that the net transmission input signal applied on the cMUT is $V_{tx}(t) = V(t)-V_{sh}+V_{dc}$, or $V_{tx}(t)=V(t)-V_{sh}-V_{dc}$, wherein $V_{tx}(t)$ defines an output signal function $V_{tx}(t)^2$ which has a dominating second-order frequency component having an output signal frequency $2\omega$; and
allowing the movable electrode of the cMUT to move in response to the applied transmission input signal to actuate the medium.

15. The method as recited in claim 14, wherein the DC bias voltage $V_{dc}$ and the shifted transmission input signal $V(t)-V_{sh}$ are applied to the same electrode of the cMUT, $V_{dc}$ is substantially the same as $V_{sh}$ to cancel each other, such that $V_{tx}(t)=V(t)-V_{sh}+V_{dc}$ is approximately the same as the $V(t)$.

16. The method as recited in claim 14, wherein the DC bias voltage $V_{dc}$ and the shifted transmission input signal $V(t)-V_{sh}$ are applied to the opposite electrodes of the cMUT, $V_{dc}$ is substantially the same as $-V_{sh}$ to cancel each other, such that $V_{tx}(t)=V(t)-V_{sh}-V_{dc}$ is approximately the same as the $V(t)$.

17. The method as recited in claim 14, wherein generating the voltage signal $V(t)$ comprises amplifying an interim voltage signal $V_{int}(t)$.

18. The method as recited in claim 14, further comprising:
generating an initial voltage signal $V_i(t)$ having a voltage swing from $-V_i$ to $+V_i$;
converting the initial voltage signal $V_i(t)$ to an absolute-value voltage signal $|V_i(t)|$ having a voltage swing from 0 to $V_i$;
generating an interim voltage signal $V_{int}(t)$ by shifting the absolute-value voltage signal $|V_i(t)|$ to obtain the interim voltage signal $V_{int}(t)$ as defined by $|V_i(t)|-Vs$; and
amplifying the interim voltage signal $V_{int}(t)$ to obtain the voltage signal $V(t)$.

19. A capacitive micromachined ultrasonic transducer (cMUT) system comprising:
a cMUT having a first electrode and a second electrode;
at least one of a transmission input signal port and a reception signal port connected to one of the first electrode and the second electrode, wherein the transmission input signal port is adapted for applying a transmission input signal to the cMUT in a transmission mode, and the reception signal port is adapted for receiving an output signal from the cMUT in a reception mode;
an AC signal source for generating the transmission input signal to be applied to one of the first electrode and the second electrode of the cMUT; and
a DC signal source for providing a DC bias voltage to be applied to one of the first electrode and the second electrode of the cMUT, wherein, when applied, the transmission input signal and the DC bias voltage together result in a total transmission input signal $V_{tx}(t)$ having a base frequency $\omega$, and wherein $V_{tx}(t)$ defines an output signal function $V_{tx}(t)^2$ which has a dominating second-order frequency component having an output signal frequency $2\omega$.

20. The cMUT as recited in claim 19, wherein the DC signal source and the DC bias voltage is switchably connected to the cMUT, the DC bias voltage being disconnected to the cMUT in the transmission mode.

* * * * *